United States Patent
Dieck et al.

(10) Patent No.: US 6,953,465 B2
(45) Date of Patent: Oct. 11, 2005

(54) CONTAINERS AND METHODS FOR DELIVERING VASO-OCCLUDING FILAMENTS AND PARTICLES

(75) Inventors: Martin S. Dieck, Cupertino, CA (US); Ryan K. Pierce, Mountain View, CA (US); Richard A. Helkowski, Redwood City, CA (US); John Miller, Redwood City, CA (US)

(73) Assignee: Concentric Medical, Inc., Mountain View, CA (US)

( * ) Notice: Subject to any disclaimer, the term of this patent is extended or adjusted under 35 U.S.C. 154(b) by 0 days.

(21) Appl. No.: 10/106,483

(22) Filed: Mar. 25, 2002

(65) Prior Publication Data

US 2003/0181931 A1 Sep. 25, 2003

(51) Int. Cl.[7] ............................................... A61B 17/08
(52) U.S. Cl. ..................... 606/157; 606/158; 606/191
(58) Field of Search ................. 606/191, 194; 604/52, 57; 623/17.12, 17.11, 17.16

(56) References Cited

U.S. PATENT DOCUMENTS

| | | | | |
|---|---|---|---|---|
| 3,585,996 | A | * | 6/1971 | Reynolds ................. 128/214.4 |
| 4,588,160 | A | * | 5/1986 | Flynn et al. .................... 251/10 |
| 4,994,069 | A | * | 2/1991 | Ritchart et al. ............. 606/191 |
| 5,382,260 | A | | 1/1995 | Dormandy, Jr. et al. |
| 5,476,472 | A | | 12/1995 | Dormandy, Jr. et al. |
| 5,660,205 | A | * | 8/1997 | Epstein .................. 137/512.15 |
| 5,964,744 | A | | 10/1999 | Balbierz et al. |
| 6,004,295 | A | * | 12/1999 | Langer et al. .............. 604/164 |
| 6,053,900 | A | | 4/2000 | Brown et al. |
| 6,113,629 | A | * | 9/2000 | Ken .............................. 623/1.1 |
| 6,129,761 | A | * | 10/2000 | Hubbell ........................ 623/11 |
| 6,166,130 | A | | 12/2000 | Rhee et al. |
| 6,203,547 | B1 | | 3/2001 | Nguyen et al. |
| 6,240,960 | B1 | * | 6/2001 | Fillmore ..................... 137/607 |
| 6,281,263 | B1 | | 8/2001 | Evans et al. |
| 6,296,632 | B1 | * | 10/2001 | Luscher et al. ........... 604/890.1 |
| 6,312,421 | B1 | * | 11/2001 | Boock ......................... 604/509 |
| 6,315,753 | B1 | * | 11/2001 | Cragg et al. .................. 604/15 |
| 6,355,014 | B1 | * | 3/2002 | Zadno-Azizi et al. ..... 604/99.02 |
| 6,485,473 | B1 | * | 11/2002 | Lynn .......................... 604/256 |
| 2002/0107502 | A1 | * | 8/2002 | Hung et al. ................. 604/506 |

OTHER PUBLICATIONS

Doxorubicin Hydochloride (Adriamycin®) The Cancer-BACUP Factsheet. http://www.cancerbacup.org.uk/info/adriamycin.htm (visited on Jul. 5, 2002).

EmboGold–http://www.biospheremed.com/embo.html (visited on Apr. 10, 2002).

Polyacrylonitril at a Glance–http://www–org.usm.edu/~lisproj/polymer/macrog/pan.html (visited on Feb. 6, 2002).

Zoltek–http://www.zoltek.com/carbon_fiber_products/ (visited on Feb. 6, 2002).

\* cited by examiner

*Primary Examiner*—David O. Reip
*Assistant Examiner*—Charles H. Sam
(74) *Attorney, Agent, or Firm*—Townsend and Townsend and Crew LLP; James M. Heslin, Esq.

(57) ABSTRACT

This is directed to containers and methods for holding and delivering vaso-occluding materials such as hydrogel particles and filaments. The vaso-occlusive materials may be held in the container in a hydrated or unhydrated state. The container includes a fluid ingress port and a fluid egress port that are respectively fluidly connectable with a fluid source and a delivery catheter. The container further includes at least one chamber or passageway extending therebetween. The passageway may be straight, curved, spiral, helical, narrow or otherwise shaped. The chamber may also have sections of varying cross section such as a ramped section. The shapes of the passageways of the container help organize ejection of the vaso-occluding materials minimizing contamination and clumping. Methods for holding and introducing the materials are also provided.

38 Claims, 10 Drawing Sheets

CONTAINERS AND METHODS FOR DELIVERING VASO-OCCLUDING FILAMENTS AND PARTICLES

TECHNICAL FIELD

This is directed to containers and methods for holding and delivering vaso-occluding filaments and particles.

BACKGROUND

Numerous persons experience some form of hemorrhagic stroke or blood vessel rupture in the brain. Ruptures can occur with a number of abnormalities including arterio venous malformations (AVM), aneurysms (a ballooning of the arterial wall), fistulas, or a burst blood vessel. Additionally, abnormal vasculature is generated in the process of tumor growth requiring larger than normal blood flow to sustain the tumor.

Various endovascular therapies for treating vessel ruptures and blood flow abnormalities include implanting vaso-occlusive agents, coils and other devices such as that described in U.S. Pat. No. 4,994,069.

Another approach to treat abnormal blood flow includes injecting hydrogel vaso-occluding particles and filaments into the vessels to be treated as described in Provisional Application Serial Nos. 60/288,458 and 60/288,494 both of which are hereby incorporated by reference in their entirety.

Injecting vaso-occluding materials, however, requires careful handling in order to avoid various problems. 1.) The particles and filaments may clump and clog the lumens and openings of the dispensing containers and instruments. 2.) The small size of the particles and filaments makes them inconvenient for a doctor to handle. In particular, capturing/collecting a filament in a solution is difficult due to their small size. 3.) The vaso-occluding material may be contaminated during the mixing or transporting step. 4.) The vaso-occluding materials may become damaged during shipping and storing. For example, when filaments are shipped in an unhydrated state, they tend to be brittle. Such filaments are particularly vulnerable to breaking during shipping.

We describe a container and procedure that will aid in preventing degradation of the physical shape of the particles and filaments during handling and shipping.

SUMMARY OF THE INVENTION

Described herein are kits, containers and methods for holding and delivering vaso-occluding particles. In one variation, the kit comprises a plurality of hydratable vaso-occluding particles and a container holding the hydratable vaso-occluding particles. The container has an ingress port and an egress port. At least one of the fluid ingress and egress ports is adapted to fluidly connect with a fluid source. The fluid ingress port may be configured for receiving liquid to hydrate the vaso-occluding particles and the fluid egress port may be configured for the liquid and the vaso-occluding particles to exit.

The container may also include at least one chamber or passageway to hold the particles. The passageway or chamber may be variously shaped. For example, the passageway may be straight, curved, conical, narrow, spiral, helical and otherwise shaped. The container may have multiple sections and the sections may have varying cross sectional areas. The various constructs of the chamber facilitate introduction of the particles into a delivery catheter.

Also, the characteristics of the particles may vary. In one variation, the particles have an outer diameter in the range of 40 microns to 2 mm and perhaps, 100 to 1400 microns. The particles may comprise polyacrylonitrile. Additionally, they may be spherical shaped and provided in a hydrated or unhydrated state.

In another variation, the container includes a mixing member. The mixing member may be elongate and have a portion that contacts and moves the particles when the mixing member is rotated.

Another container includes a conical distal end section. The conical distal end section decreases in diameter towards the fluid egress port. The conical portion may be sized to fit within the proximal end of a delivery catheter.

Another container includes at least one fluid relief port and at least one fluid relief passageway fluidly connected with the fluid relief port. The fluid relief port may have a size smaller than that of the particles such that the particles cannot pass therethrough. The fluid relief passageways may extend to the fluid egress port such that liquid driven through the container flows through the chamber and the fluid relief passageway while the particles are permitted only to flow through the chamber.

In another variation, the container may include at least one one-way valve.

In another variation, the container includes a membrane or screen. For example, the container may comprise a first chamber in fluid communication with an ingress port and a second chamber in fluid communication with an egress port. The first chamber and the second chamber may be separated by a support member having at least one opening larger than the vaso-occluding particles or filaments. When the opening is not covered, fluid and the occluding materials may pass through. The container may further comprise a movable screen positioned across the support and the screen may include at least one particle-blocking section and at least one particle-passing section. The particle-blocking section has a plurality of apertures smaller than the particles and the particle-passing section has at least one aperture larger than the particles. The screen is movable such that when the particle-passing section of the movable screen is aligned with the opening of the support the particles may enter the second chamber. Also, when the particle-passing section of the movable screen member is not aligned with the opening of the support the particles may not enter the second chamber.

In another variation, the container may include a fluid outlet and a screen member disposed across the outlet. The screen member may be fixed and the outlet may be covetable. The screen member may have a plurality of apertures and each of the apertures is smaller than the particles or filaments such that the particles may not pass through the outlet.

A kit may also include a cap to cover one of the fluid ingress and fluid egress ports. Additionally, the fluid ingress and fluid egress ports may have Luer-type or other threaded fitting to fluidly connect the syringe and delivery catheter to the container.

Another kit comprises a hydratable filamentary occluding material and a container holding the material. The material may comprise polyacrylonitrile. The container may have a first opening for fluid flow and a second opening for fluid flow and exit of the filamentary occluding material. At least one of the openings may be adapted for connection to a fluid source such as a syringe.

Also, one of the first and second openings may be adapted for connection with a delivery catheter. The container may further include at least one chamber or passageway to hold the fluid and the filaments.

The passageway or chamber may be variously shaped. For example, the passageway may be straight, curved, conical, narrow, spiral, helical and otherwise shaped. The container may have multiple sections and the sections; may have varying cross sectional areas. The various constructs of the chamber facilitate introduction of the particles into a delivery catheter.

In another variation, the passageway of the container is configured to allow only one filament of occluding material pass therethrough at a time. The diameter of the passageway may be in the range of 100 um to 5 mm.

Also, the shape of the container itself may vary. The container may have, for example, a disk-, card-, cylindrical-, or turnip-shape. The container may also include a screen or membrane. The membrane may have openings sized to prevent the filament material from passing thereftrough but allow liquid to pass therethrough.

Another container includes a rotatable barrel. The barrel may have multiple passageways for holding filaments and a body having a single ejection channel. To deliver a selected filament, one of the multiple passageways is aligned with the channel such that a fluid pathway is formed from the fluid source to the egress port of the container.

A method for holding and introducing vaso-occluding materials into a delivery catheter is also provided herein. The method may include the steps of hydrating the material in a container and pushing at least a portion of the material from the container, to a target site. The pushing step may be performed using fluid pressure or a displacing member. The occluding materials may be a filament.

The method may also include the additional step of breaking the filament at a selected location along the length of the filament. The breaking may be performed by pinching the filament. The pinching may be performed using an expandable balloon. Also, the breaking may be performed using a noose or snare.

Yet another method includes an additional step of detecting discrete sections of the filament along its length. The sections may be marked or enlarged to provide information or feedback to a doctor or physician. The filament may then be broken at a selected point upon detecting a certain number of segments. The point of detachment may be distal or proximal to the distal end of the catheter and perhaps, within the container.

DETAILED DESCRIPTION

Described below are containers and methods for holding and delivering vaso-occluding materials to a target site.

Figure 1:
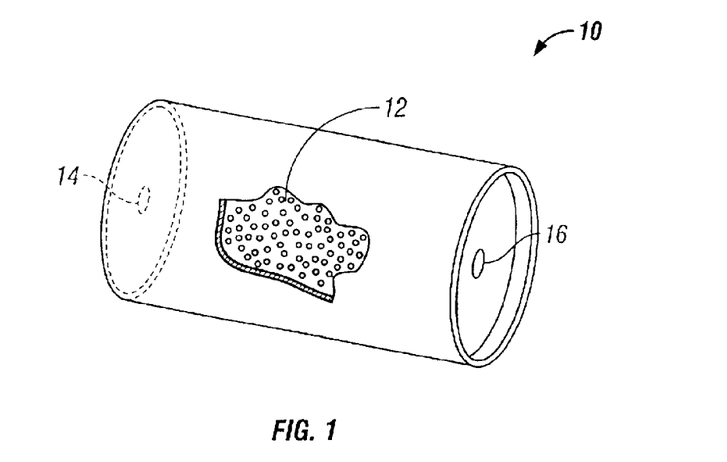
FIG. 1 is a perspective view of a container.
Figure 2:
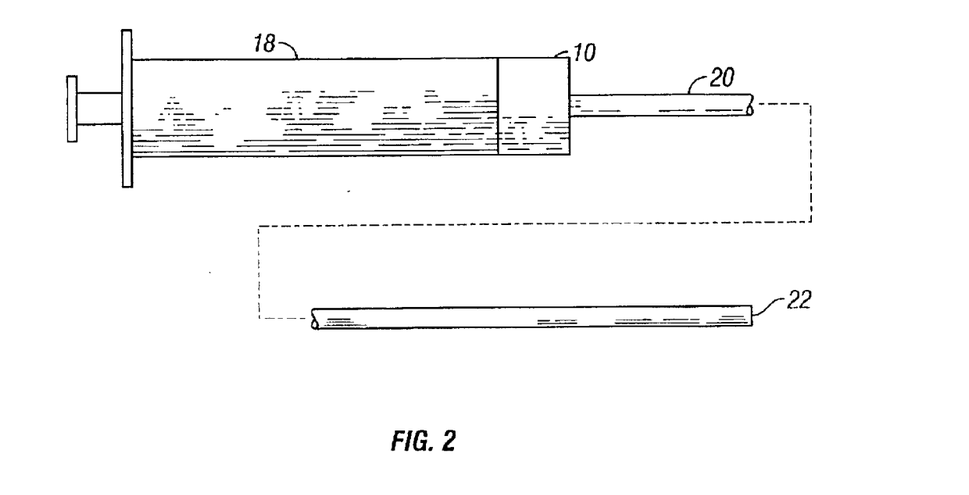
FIG. 2 is an illustration of a catheter assembly.

FIGS. 1-2 illustrate one variation of a container. In particular; a barrel-shaped container (10) is shown holding vaso-occluding materials (12) described further below. The container (10) includes a fluid ingress port (14), which can be removably connected to a fluid source such as a syringe (18). The container (10) further includes a fluid egress port (16) which can be removably connected with a vaso-occlusive delivery device such as delivery catheter (20). During operation, fluid pressure from the syringe drives the vaso-occluding materials from the container (10) into the delivery catheter (22). Fluid pressure is further supplied to urge the vaso-occluding materials through the delivery catheter and out its distal end (22). In this manner, vaso-occluding materials are delivered to a target site. Target sites include, but are not limited to, the abnormal vasculature of a tumor, aneurysms and other sites of abnormal blood flow as well as vessels, ducts and cavities that are not part of the blood vascular system.

Vaso-occluding Materials

The containers described herein may hold and introduce vaso-occluding materials into a delivery catheter. The vaso-occluding materials include but are not limited to (1.) vaso-occluding particles (e.g. biocompatible polymeric microspheres) and (2.) vaso-occlusive filamentary materials (e.g., hydrophilic polyacrylonitrile or HYPAN). The vaso-occluding materials may be made from a variety of substances including hydrogel polymers and polymers. Examples of hydrogel polymers and polymers include: polyacrylamide (PAAM), poly (N-isopropylacryl amine) (PNIPAM), poly (vinylmethylether), poly (ethylene oxide), poly (vinylalcohol), poly (ethyl (hydroxyethyl) cellulose), poly(2-ethyl oxazoline), Polylactide (PLA), Polyglycolide (PGA), Poly(lactide-co-glycolide) PLGA, Poly(e-caprolactone), Polydiaoxanone, Polyanhydride, Trimethylene carbonate, Poly(β-hydroxybutyrate), Poly(g-ethyl glutamate), Poly(DTH-iminocarbonate), Poly(bisphenol A iminocarbonate), Poly(orthoester) (POE), Polycyanoacrylate (PCA), Polyphosphazene, Polyethylenoxide (PEO), Polyethlglycol (PEG), Polyacrylacid (PAA), Polyacrylonitrile (PAN), Polyvinylacrylate (PVA), Polyvinylpyrrolidone (PVP), a co-polymer of two or more polymers, and a blend of two or more polymers.

The hydrogel polymer or polymers may also comprise a natural polymer. Examples of natural polymer include collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, elastin and copolymers and blends of the polymers.

Also, the materials may comprise a bioactive agent and or a radio-pacifier to facilitate visualization of the vaso-occluding materials at a target site.

Another particular material which may be used in conjunction with the containers described herein is a hydrogel filament. In one variation, the filament is comprised of an extruded polyacrylonitrile.

One way of fabricating such a filament is by the process of dissolving the polyacrylonitrile in DMSO and extruding it into an alcohol bath, whereupon the polyacrylonitrile solution forms a filament. The filament is then removed from the alcohol (e.g. isopropyl or like alcohol) and allowed to dry. Prior to implantation in a patient the filament may be hydrated. Alternatively, the filament maybe stored in a hydrated state. The filament can then be injected or delivered in a delivery tool to a chosen site in the patient. The hydrated filament forms a vaso-occlusive filamentous mass and occludes normal flow.

Dimensions for the vaso-occlusive devices may be as desired for a specific purpose, but generally would be in a range from about 0.005 inches to about 0.50 inches. The diameter of the occluding particles may be in the range of 40 um to 2 mm and perhaps 100 um to 1400 um. The occluding filamentary materials may have a diameter in the range of 100 um to 5 mm and perhaps, 100 um to 2 mm. Also, the diameter of the vaso-occlusive materials may be selected such that they may pass through a delivery device such as a delivery catheter. The lengths of the vaso-occlusive device as delivered may be generally in the range from about 1 mm to about 5 meters. The diameter of the vaso-occlusive device once it is delivered and after it has assumed its vaso-occluding shape may be in a range from about 0.1 mm to about 50 mm.

A description of particular hydrogel materials maybe found in Provisional Patent Application Nos. 60/288,458 entitled "Hydrogel Filament Vaso-occlusive Device" and 60/288,494 entitled "Hydrogel Vaso-Occlusive Device" both filed May 4, 2001, both of which are hereby incorporated by reference in their entirety.

Procedural Overview of Vaso-occluding Treatments

Figure 3A:
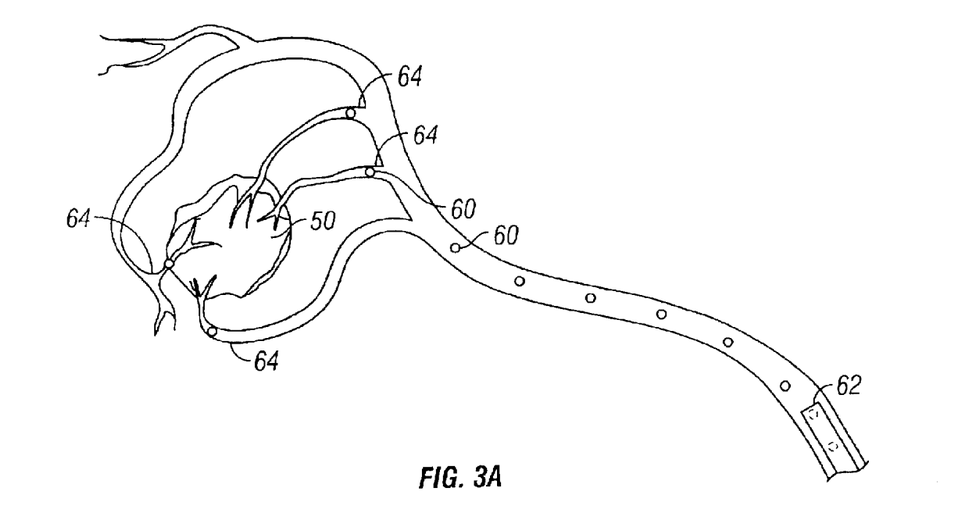
FIG. 3a is an illustration of an application showing vaso-occluding particles being delivered to a plurality of blood vessels for treatment of a tumor.

FIGS. 3a-3b show examples of deploying vaso-occlusive particles. Referring to FIG. 3a, a tumor (50) is shown being treated with vaso-occluding particles (60). In particular, vaso-occluding particles such as the hydrogel particles discussed above are shown being delivered from a delivery catheter (62) to various blood vessels (64) supplying blood to the tumor (50). The vaso-occluding particles form blockages in the vessels (64) leading to the tumor. Accordingly, the blood to the tumor is cut off, inhibiting tumor growth.

Figure 3B:
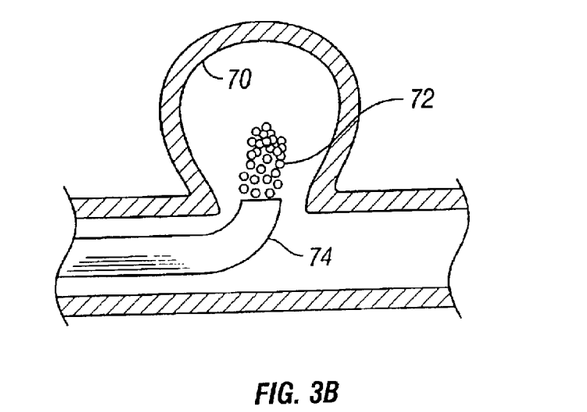
FIG. 3b is an illustration of another application showing vaso-occluding particles being delivered to an aneurysm.

FIG. 3b illustrates treatment of an aneurysm (70). In FIG. 3b, vaso-occluding particles (72) are delivered into the aneurysm (70). The vaso-occluding particles form an occlusive mass in the aneurysm, minimizing its undesirable effects on the artery.

Also, instead of (or in addition to) vaso-occluding particles, occluding filaments may be supplied to form blockages in the vessels or an occlusive mass in the aneurysm.

It is to be understood, however, that the containers and occluding materials described herein are not limited to occluding blood vessels or aneurysms. Rather, the containers and occluding materials described herein may be used to form occlusions in any of the vessels, ducts, and cavities found in the body including but not limited to vessels found in the blood vasculature.

In both FIGS. 3a and 3b, the distal tip of a delivery catheter (62, 74) is positioned near the target site via a catheterization procedure. One catheterization procedure for treatment of various vascular defects includes inserting a sheath into an artery such as the femoral artery. Inserting a guidewire into the sheath and advancing the guidewire to the desired site such as a tumor or aneurysm. Next, a catheter assembly including an elongate introduce catheter is inserted into the sheath and the catheter assembly is advanced over the guidewire to the target site. Once the catheter assembly is property positioned at the target site, the guidewire is removed from the introducer catheter. A delivery catheter is then inserted within the introducer catheter until the distal end of the delivery catheter is positioned at the site to be embolized. Vaso-occluding materials are fed into the delivery catheter and delivered to the treat site.

Additional examples of catheter assemblies are discussed in, for example, U.S. Pat. Nos. 5,382,260 and 5,476,472. Also, other catheter assemblies known to those of skill in the art may be used in conjunction with the delivery devices and occluding materials described herein. Devices and methods for treating aneurysms and the like are also described in U.S. Application No. 10/106,870, filed Mar. 25, 2002 entitled "Devices And Methods For Treating Vascular Malformations" by Sepetka et al. which is a continuation in part application of U.S. Application Ser. No. 09/695,637, filed Oct. 24, 2000, which is a continuation in part of U.S. Application Ser. No. 09/324,359 filed Jun. 2, 1999, each of which is incorporated by reference in its entirety.

Figure 4:
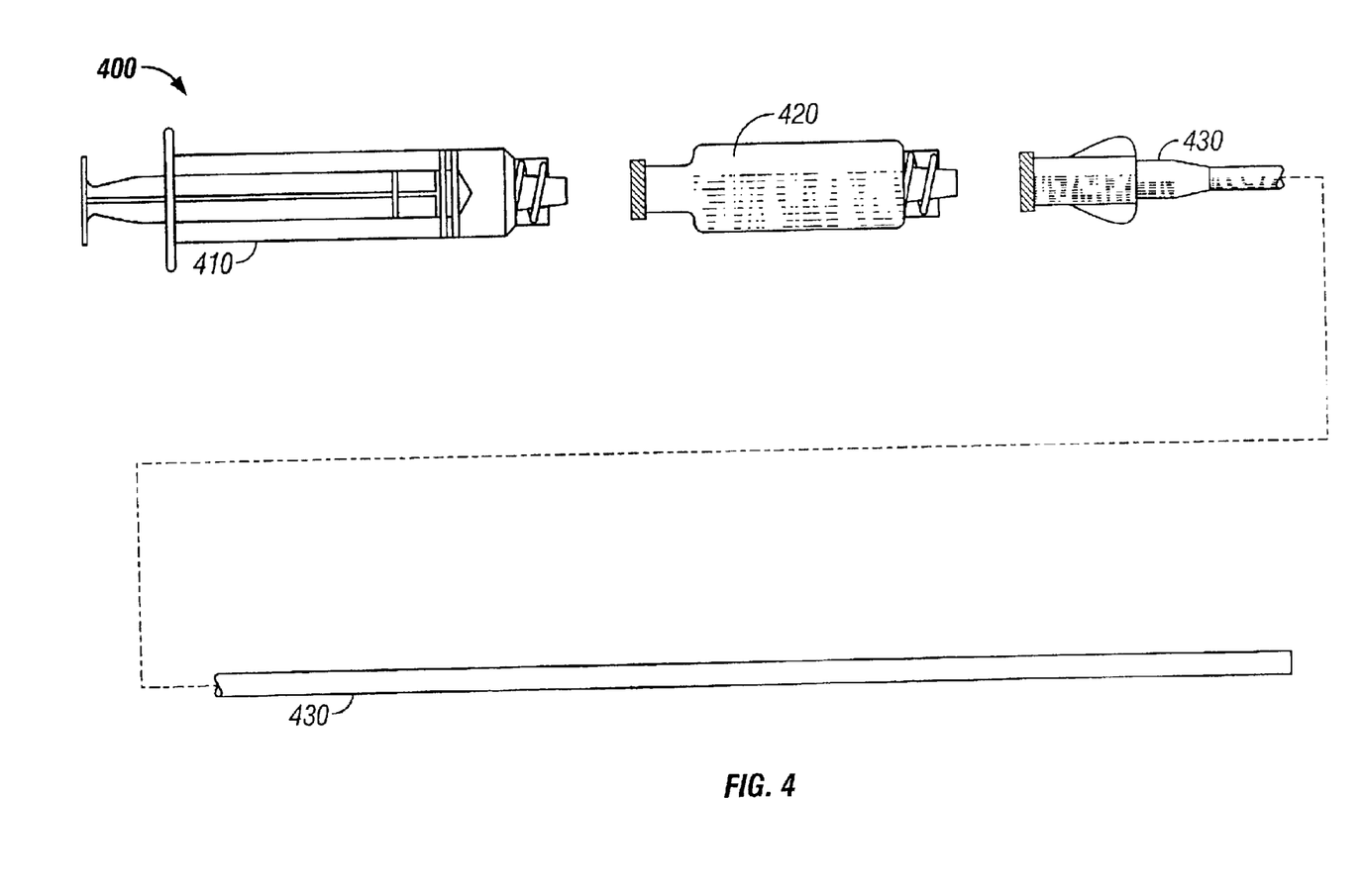
FIG. 4 is an exploded view of a catheter assembly.

Vaso-occluding materials may be delivered to a treatment site through a delivery catheter. An example of a particular delivery catheter assembly (400) for use with the present invention is shown in FIG. 4 and includes a syringe (410), a cartridge or container (420) and a delivery catheter (430). The delivery catheter assembly shown in FIG. 4 shows the cartridge separated from the syringe. However, the invention is not so limited and the cartridge may be integrally connected with the syringe. In yet another variation, the cartridge is integral with the delivery catheter (430). Kits may also be provided having a cartridge with a plurality of vaso-occluding particles and or a hydrating liquid contained therein.

To reiterate, these various containers and cartridges may be connectable with a delivery catheter. As described, vaso-occluding materials held in the containers may be hydrated, washed, or mixed in the container. The vaso-occluding materials may then be injected into the delivery catheter by fluid pressure or some other way such as by use of a displacement wire for implantation at in a target treatment site. The containers may have fluid ingress and egress ports and at least one passageway connecting the fluid ingress port to the fluid egress port. The shapes, number of passageways, and other features of the containers may take various configurations, discussed below.

Containers for Holding Vaso-occluding Particles

Figure 5A:
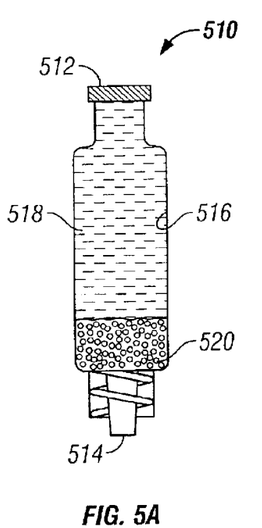
FIGS. 5a-5n are partial cross sectional views of various containers for holding vaso-occluding particles.

FIG. 5a illustrates a container (510) having a cylindrical shape for holding vaso-occlusive materials. The container includes a fluid ingress port (512) and fluid egress port (514). The fluid ingress port and the fluid egress port are adapted to fluidly connect the container to a syringe and delivery catheter respectively. The ends of the container may have Luer-type fittings for convenient assembly with the syringe and delivery tool.

In this variation, the container includes a chamber or passageway (516) fluidly connecting the fluid ingress port and the fluid egress port. A liquid (518) and vaso-occluding particles (520) are held in the chamber (516). The particles are urged towards the fluid egress port (514) by fluid pressure and flow. The vaso-occluding particles are injected into, for example, a delivery catheter (not shown) through the fluid egress port.

The container may be made of various materials such as but not limited to polymers, copolymers, glass, metals or alloys. For example, the container may be made of a transparent polymer material such as clear polycarbonate. The container may be fabricated in components or sections and bonded together using heat treatment, adhesives and ultrasonic welding, for example. The container and its components may be, for instance, injection molded, machined and micromachined. Other techniques for forming the container and or its components may be used as is known to those of skill in the art. The container may also comprise a variety of coatings or treatments such as a hydrophilic coating.

The dimensions of the container should be sufficient such that the containers can fluidly connect with various conventional syringes and delivery catheters. However, the dimensions may vary such that the container may be adapted to connect with other types of liquid sources (e.g., a gas line) and delivery devices.

Figure 5B:
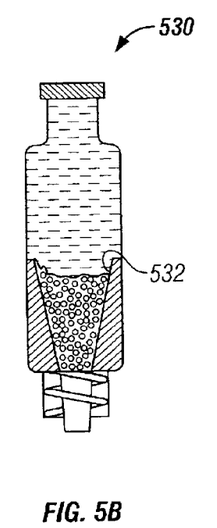

FIG. 5b illustrates another container (530). The container (530) shown in FIG. 5b differs from that shown in FIG. 5a in that the chamber includes a ramped portion 532. Ramp portion (532) focuses the vaso-occluding particles (534) at the outlet port This generally serves to "meter" the particles as they are ejected from the container, preventing clumping.

Figure 5C:
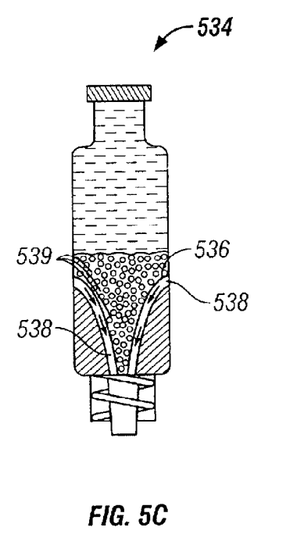

FIG. 5c illustrates another container (534) also having a ramped portion (536). However, in this variation, a fluid relief lumen (538) is provided along the ramped portion. A plurality of relief openings (539) fluidly connect the chamber to the fluid relief lumen. The relief openings are sized to permit only liquid (not the vaso-occluding particles) into the fluid relief lumen Accordingly, liquid may be driven through the container and into the delivery catheter regardless of the degree of particle clogging at the container outlet. In this variation, therefore, vaso-occluding particles in the catheter may be pushed through the catheter by fluid pressure regardless of the degree of particle clogging in the container.

Figure 5D:
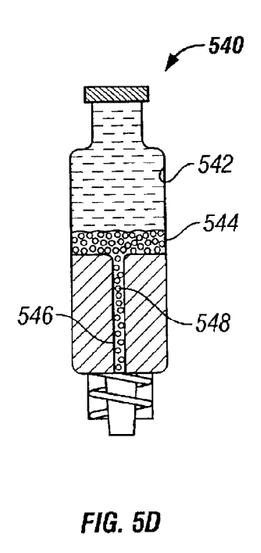

FIG. 5d illustrates another container (540) having a first chamber (542) for holding a plurality of vaso-occluding materials (544) and a passageway (546). The diameter of the passageway (546) may be adjusted to provide an optimal particle throughput. In this variation the passageway has a diameter equal to that of a particle (548). The narrow passageway (546) is to help organize the particles as they enter a delivery catheter (not shown).

Figure 5E:
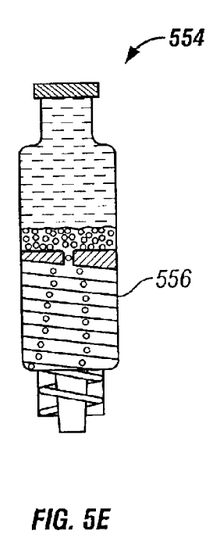

FIG. 5e illustrates yet another container (554). The container shown in FIG. 5e differs from that shown in FIG. 5d in that the container (554) of FIG. 5e includes a spiral passageway (556). Like the container shown in FIG. 5d, the container shown in FIG. 5e provides for organized particle transport and ejection.

Figure 5F:
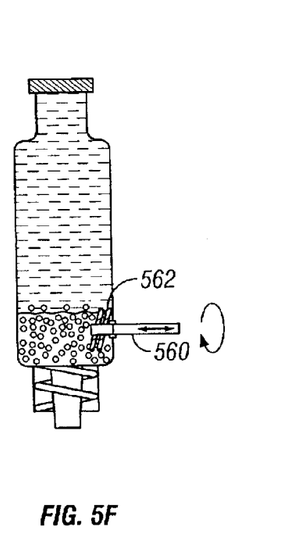

FIG. 5f illustrates yet another container. The container shown in FIG. 5f includes a mixing member (560) for displacing the vaso-occluding materials. Mixing the particles prevents the particles from clumping Mixing member (560) includes a handle portion that is outside the container and a working portion that is inside the chamber. The mixing member may also include fingers (562). The fingers (562) contact and move the vaso-occluding materials when the mixing member is moved (or rotated). The mixing member may be immovable linearly and or angularly. Accordingly, the variation shown in FIG. 5f provides a container which actively prevents clumping of vaso-occluding particles near the outlet.

Figure 5G:
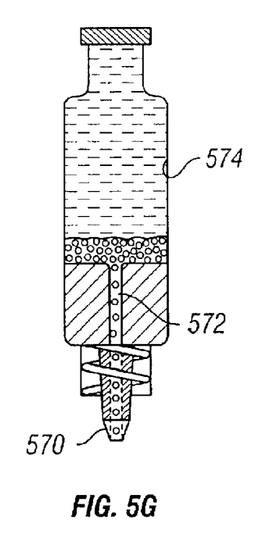

FIG. 5g illustrates a container having a constant diameter passageway (572) and a tapered distal end (570). When the container is connected with a delivery catheter, the tapered distal end (570) extends into the proximal end of the catheter. This extends the constant diameter passageway into the delivery catheter and alleviates problematic flow effects arising from the entrance of the delivery catheter.

Figure 5H:
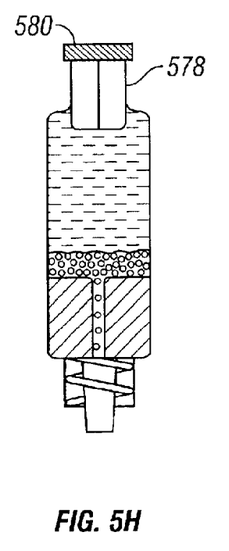

FIG. 5h illustrates another container having a one-way valve (578). The valve (578) may be a duckbill valve made of an elastomeric material which remains closed in its relaxed state. Upon applying fluid pressure from the fluid ingress port (580), the valve opens allowing fluid to pass. However, fluid and particles cannot pass the other direction. The valve may be positioned at the outlet end or at another location of the container. Also, multiple valves may be used to provide particular flow control schemes.

The vaso-occluding particles may be hydrated with a hydration liquid and the hydration liquid may be pushed through, for example, a screen or membrane or the like. A second liquid may be supplied to the container to purge the first liquid and to drive the vaso-occluding particles to a desired site. The second liquid may be a therapeutic liquid. Examples of therapeutic liquids include but are not limited to analgesics, anesthetics, antibiotics, thrombotic agents, chemotherapeutic drugs, and thrombolytic agents. A particular example is doxorubicin, which is used to treat tumors. Also, a contrast agent for visualization can be used. Accordingly, the target site can be simultaneously treated with embolizing particles and a therapeutic liquid.

Figure 5I:
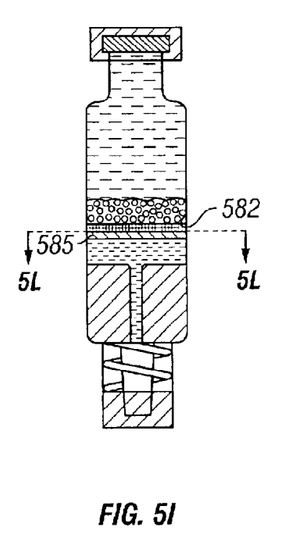

FIG. 5i illustrates a variation using a movable screen (582). The screen has openings, which allow liquid, but not particles, to pass. The screen (582) may be pie shaped as shown in FIG. 5l and it may have at least one open region (583) (or open "slice"). Also, the open region may include apertures so long as at least one of the apertures is larger than the vaso-occluding particles. When this particle-passing region (583) is aligned with an opening on a screen support such as support (585), vaso-occluding particles may pass therethrough. When the regions are not aligned, only fluid (and not the particles) may pass.

Figure 5J:
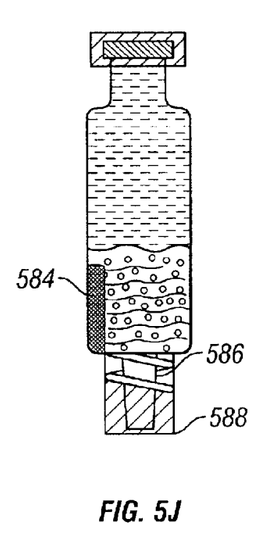

FIG. 5j illustrates a container having a fixed screen (584) and a cap (588) covering the outlet (586). The screen has openings that permit fluid, but not particles, to pass. The container shown in FIGS. 5i-5j may be used to hydrate vaso-occluding particles and provide a way to replace the hydrating fluid with a second, perhaps therapeutic fluid.

Figure 5K:
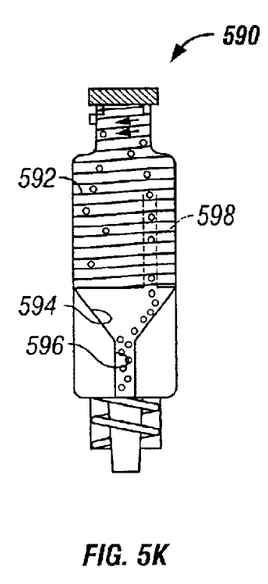
Figure 5L:
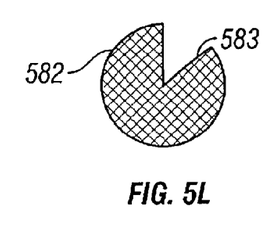

FIG. 5k illustrates another container (590). In this example, the container (590) includes a spiral passageway (592) leading to a ramped chamber (594). The ramped chamber further leads to a straight passageway (596).

The spiral passageway (592) includes at least one particle aperture (598) through which vaso-occluding particles moving along the passageway may pass. Thus, some particles fall through the apertures (598) and other particles continue down the spiral passageway (592). The particles that fall through the apertures bypass one or more turns in the spiral passageway and directly enter the ramped section (594). The ramped chamber shown in this variation is tapered and focuses the particles into a straight passageway (596) which accepts only one particle at a time. Accordingly, the container (590) focuses vaso-occluding particles into an attached delivery catheter (not shown).

Figure 5M:
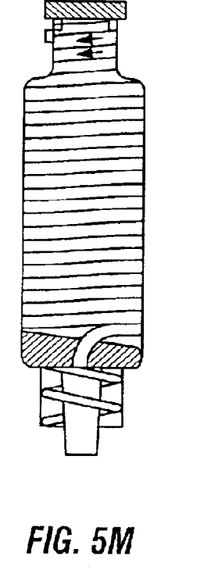
Figure 5N:
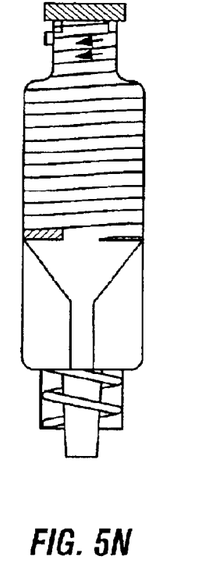

FIG. 5m shows a container having a helical passageway extending from a fluid inlet to a fluid outlet. The helical passageway of FIG. 5m, however, does not include apertures along its path so that particles (and/or filaments) stay in line along the helical path before reaching the fluid outlet. In still another variation, as shown in FIG. 5n, a helical path may lead to a ramped section which focuses the occluding materials to a fluid outlet. Accordingly, containers described herein may have helical passageways which do include apertures along their paths and helical passageways which do not include apertures along their paths. The helical passageways may extend to fluid outlets or the passageways may lead to another focussing chamber such as a ramped section, which focuses the occluding materials to a fluid outlet.

Containers for Holding Vaso-occluding Filaments

Figure 6A:
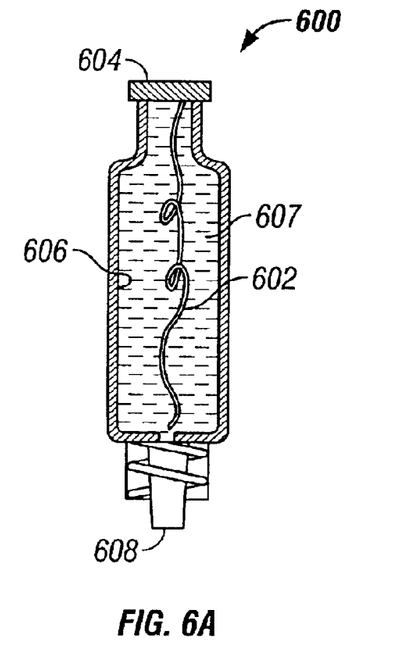
FIGS. 6a-6k are partial cross sectional views of various containers for holding vaso-occluding filaments.

The containers described herein may also hold and deliver vaso-occluding filaments. FIG. 6a illustrates a particular container (600) suitable for delivering a filament (602). Similar to the above described containers, the container shown in FIG. 6a includes an inlet (604) for receiving liquids, a passageway or chamber (606) for holding the filament and liquids (607), and an outlet (608) for ejecting the filament and or liquid. The inlet end and outlet end can be designed to fluidly connect with a fluid source (e.g., a syringe) and a delivery catheter respectively. In operation, the filament is hydrated and ejected from the outlet (608) into, for example, a delivery catheter.

The chamber shown in FIG. 6a may be cylindrical and substantially larger in diameter than the filament (602). However, the invention is not so limited and other shapes of chambers are contemplated.

Figure 6B:
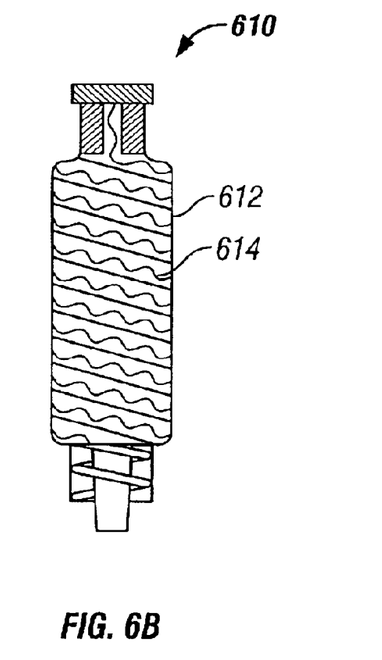

FIG. 6b illustrates another container (610) having a spiral passageway (612). The spiral passageway (612) is very space efficient and holds very long filaments in short containers. A displacement member or wire may be provided to push the filament through the passageway. The displacement wire may be a flexible metal or alloy. The displacement wire may be made of, for example, NITINOL. Such a displacement member may include markings along its length. The marks may be equally spaced to provide an idea or measure of the length of filament ejected from the distal end of the catheter.

Figure 6C:
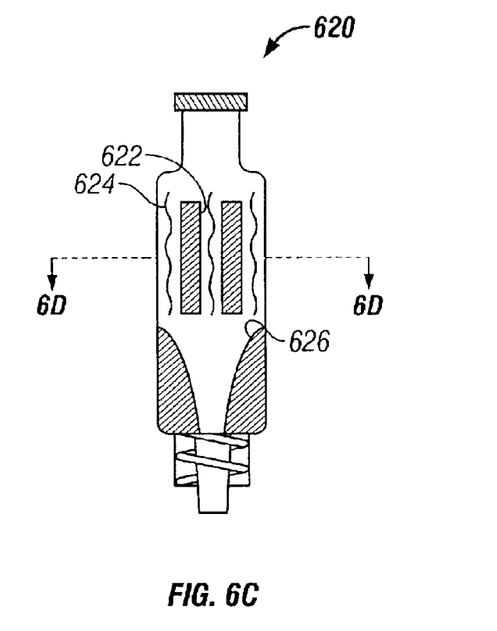
Figure 6D:
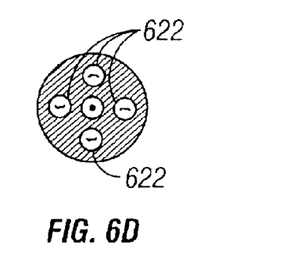

FIG. 6c shows yet another container (620) having a set of ganged passageways (622) for holding and delivering multiple filaments (624) in parallel. The container (620) shown in FIG. 6c also includes a ramped portion (626) to focus the filaments towards the delivery end. FIG. 6d shows a cross sectional view of the container along 6d-6d. This container provides for multiplexed filament delivery.

Figure 6E:
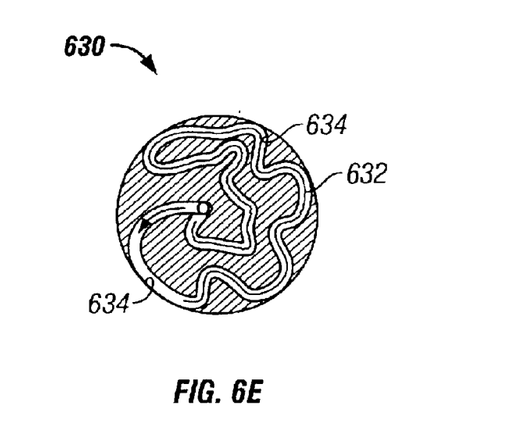
Figure 6F:
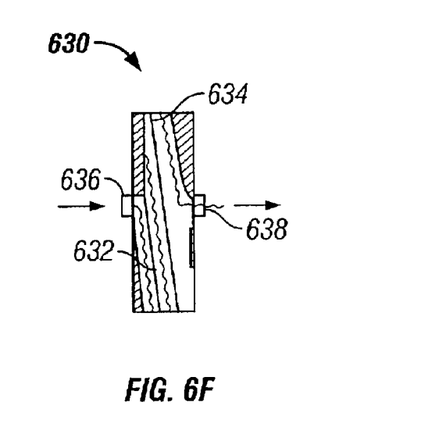

FIGS. 6e-6f illustrate another container (630) for holding filaments (632). The container (630) shown in FIGS. 6e and 6f is shaped like a disk. The container (630) includes a passageway (634) for holding and delivering a filament (632) from an inlet (636) to an outlet port (638). The passageway may be a spiral, serpentine, or other curved shape to connect the inlet (636) to the outlet (638). Also, it is to be understood that the shape of the container may vary greatly and include, for example, cylindrical, disk, rectangular, oval, turnip, and other shapes.

Figures 6G, 6H, 6I:
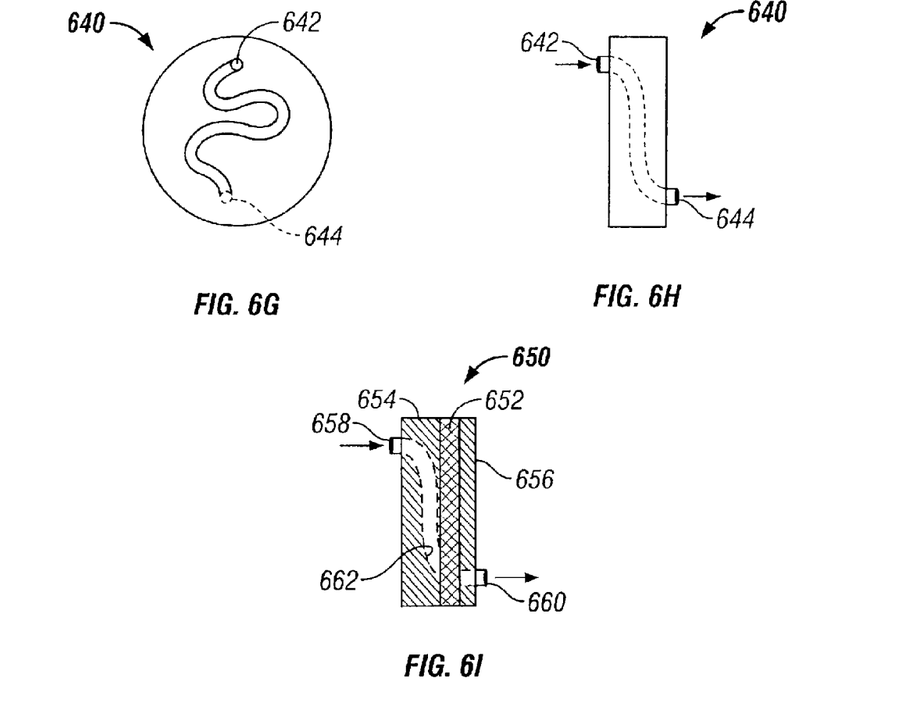

FIGS. 6g and 6h illustrate another container (640) similar in function to those shown in FIGS. 6e-6f. These figures depict a centerline of inlet (642) and the centerline of outlet (644) separated by a distance (D).

FIG. 6i illustrates yet another container (650) including a membrane (652) between a base (654) and a cover (656). The base, membrane and cover are detachably connected such that pre-selected membranes may be added or removed for various applications. Also, the components should be fluidly sealed to prevent leaks.

One application for container (650) is filament hydration. A hydrating liquid is supplied to the passageway (662) via inlet (658), hydrating the contents therein. The liquid may then be driven through membrane (652) and ejected from outlet (660). The membrane includes openings that prevent the filament from passing therethrough yet allow the hydrating liquid to pass therethrough. A variety of membranes and filters may be used to selectively allow certain substances to pass. Once the filament is hydrated, the membrane is removed and the container is connected with a delivery tool to deliver the filament to a target site.

Figure 6J:
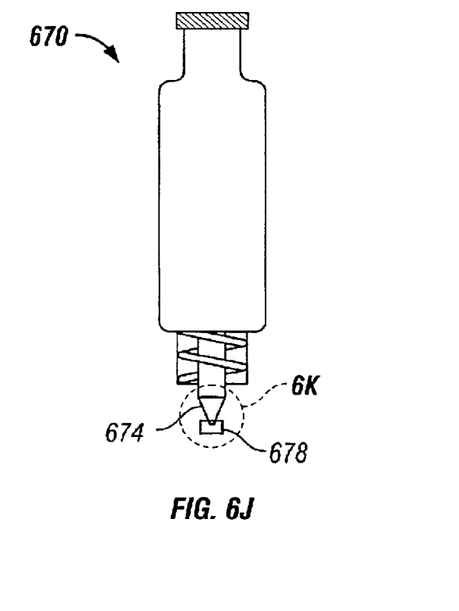
Figure 6K:
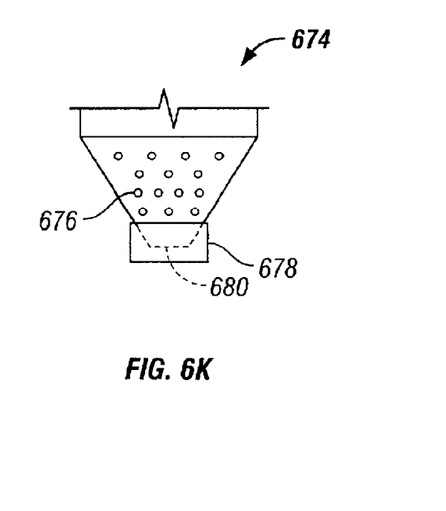

FIGS. 6j-6k illustrate yet another container (670) having a conical end section (674). The conical end section (674) has a fluid egress port allowing liquids and vaso-occluding materials to flow therethrough. The conical end section (674) is adapted to extend into (and mate) with the proximal end of a delivery catheter.

The conical distal end section (674) also includes rinse ports (676) as shown of FIG. 6k. The rinse ports (676) are sized to prevent vaso-occluding materials such as filaments and particles from flowing therethrough but allow liquid to pass therethrough.

An application for container (670) is filament hydration and delivery. A hydrating liquid is injected into the container. The hydrating liquid hydrates the filament, and exits through the rinse ports (676). The vaso-occluding materials, however, are prevented from passing through the rinse ports due to their size and are prevented from passing through the egress port (680) due to the cap (678). Once the filaments are hydrated, a second liquid can be supplied to the container purging the hydrating liquid from the system. The cap may then be removed and the container may be connected with a catheter assembly.

The distal end section (674) may be designed such that the rinse ports (676) are covered by the delivery catheter entrance (not shown) when the catheter is connected with the container. In particular, the conical section (674) extends into the catheter hub such that the rinse ports (676) are covered. Accordingly, vaso-occluding materials and or liquids are forced to pass through the fluid egress port (680) and into the delivery catheter.

Rotatable Multipassageway Container

Figure 7A:
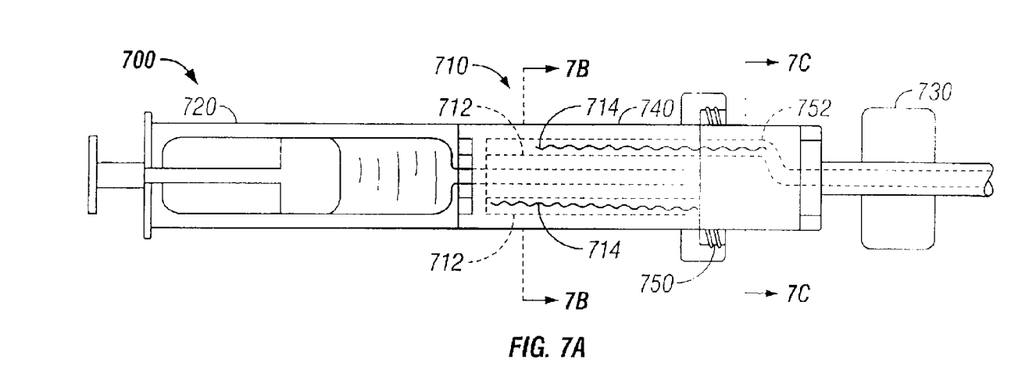
FIG. 7a is a partial cross sectional view of another catheter assembly having a rotatable multipassageway container.
Figure 7B:
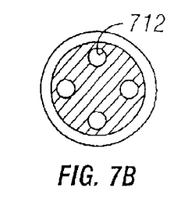
FIG. 7b is a cross sectional view of the container shown in FIG. 7a taken along line 7B—7B.
Figures 7C, 7E:
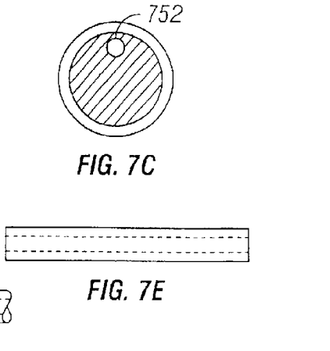
FIG. 7c is a cross sectional view of the container shown in FIG. 7a taken along line 7C—7C.
FIG. 7e is a cross sectional view of the container shown in FIG. 7d taken along line 7E—7E.

FIGS. 7a-7c show several views of a delivery catheter assembly having a rotatable multipassageway container (710). In this variation, a catheter assembly (700) includes a container (710) having a plurality of passageways (712) for holding filaments (714), a syringe (720) for supplying fluid to the container to hydrate and drive the filaments, and a delivery catheter (730) for delivering the filaments to a target site.

The container shown in FIG. 7a includes a revolving barrel (740). The barrel revolves about a central axis. The revolving barrel includes a plurality of passageways (714). The passageways are circumferentially positioned along a circle. See, for example, FIG. 7b. Each passageway (714) is configured to hold vaso-occluding filament. The passageways may take various shapes and be, for example, straight or curved.

The revolving barrel also has a fluid inlet port that is fluidly connected with a syringe. The barrel further has a distal end and the passageways extend to the distal end, defining an equal number of filament exit ports. There are four passageways shown in this figure but the invention is not so limited and the barrel may have more or less passageways.

The container also includes a body (750), which fluidly connects one of the passageways (714) with the proximal end of the delivery catheter (730). The body includes one channel (752) which can align (or register) with a selected passageway of the plurality of passageways (714). See also FIG. 7c. Once a passageway is aligned with the channel a complete fluid pathway is formed from the syringe to the delivery catheter. Accordingly, a selected filament may be ejected from the container into the delivery catheter.

It is to be understood that while the above described variation shows the barrel and syringe being rotatable, the invention is not so limited. Other members may be rotated to achieve a complete fluid pathway for filament delivery. Also, the container may be "closed" by adjusting the barrel such that no passageways are aligned with the channel, fluidly sealing each passageway.

Figure 7D:
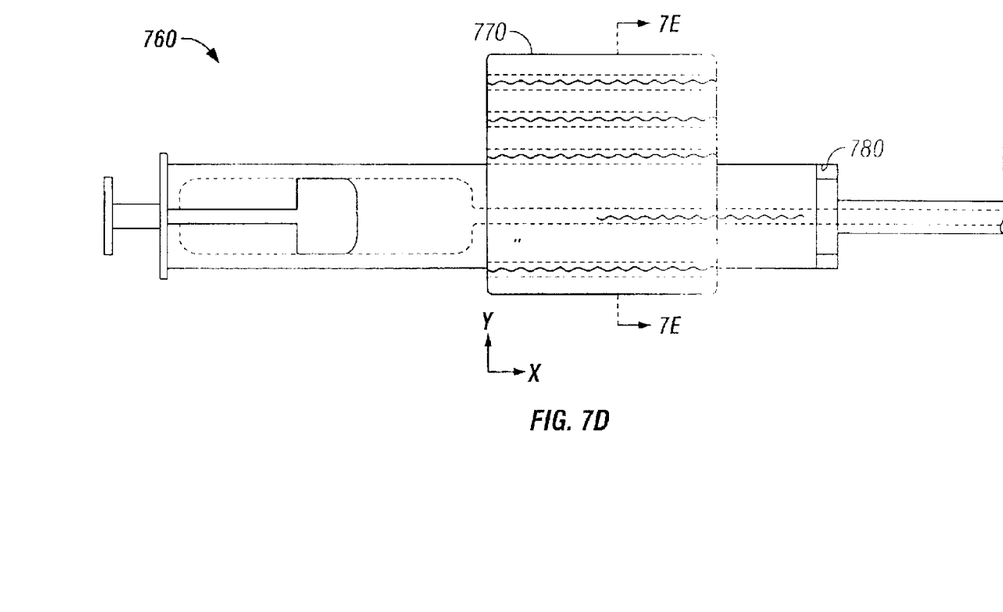
FIG. 7d is a cross sectional view of yet another catheter assembly having a planar-shaped multipassageway container.

FIGS. 7d and 7e show another catheter assembly (760) having a movable multichamber container (770). This variation is different than the above barrel shaped variation in that it is card-shaped. Also, the container moves in a plane such as the XY plane. The passageways from the movable device are aligned with a channel of the body component (780) to create a fluid path connecting the syringe to the delivery catheter. Accordingly, filaments may be pushed through the container and to the target site.

Filament Length Control

When delivering vaso-occluding filaments to a target site, it is sometimes desirable to break or sever the filament. For example, in selecting a specific size filament for filling an aneurysm it is desirable to break the filament at a certain location along the length of the filament. Various techniques for breaking the filaments are described herein.

Figure 8A:
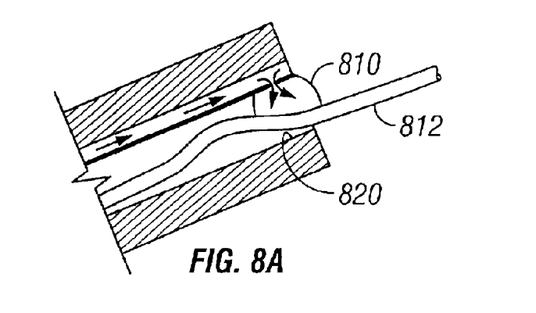
FIGS. 8a-8d are illustrations of various techniques for breaking or severing a filament.
Figure 8B:
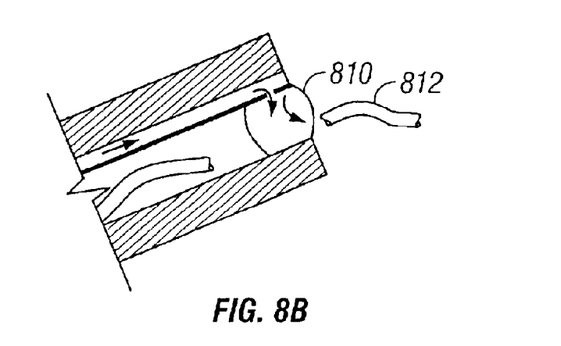

One technique for severing a filament is shown in FIGS. 8a and 8b. These figures depict inflating a balloon member (810) to pinch a filament (812) between the balloon and the inner wall (816) of a delivery catheter. As the balloon member expands it continues to pinch the filament until the filament severs.

Figure 8C:
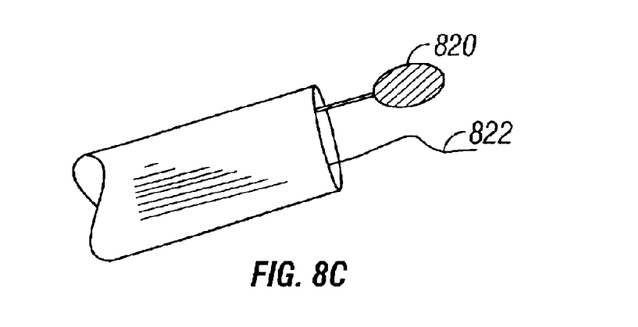

Another "pinching" technique is shown in FIG. 8c. In FIG. 8c, an enlarged member (820) is provided. When the enlarged member (820) is moved proximally, it pinches the filament (822) against the delivery catheter wall, breaking the filament. The enlarged member may have a ball shape. The enlarged member may also be, for example, a knot.

Figure 8D:
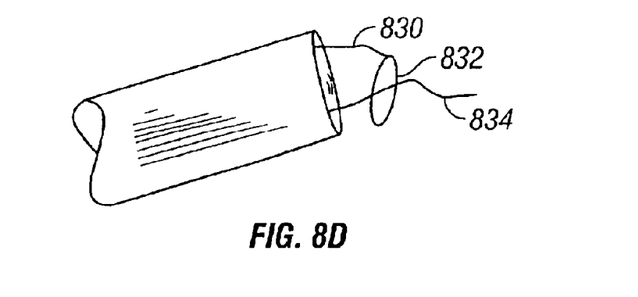

Another technique for breaking a length of filament is shown in FIG. 8d. In particular, a noose (832) surrounds the filament (834) at a selected location. The noose (832) is tightened by pulling the member (830) thereby breaking the filament. An exemplary snare device is shown in U.S. Pat. No. 6,312,421 to Boock.

Still other techniques for breaking the filament include providing the filament with a detachable joint The detachable joint may be activatable or dissolvable upon receiving various stimuli such as, for example, blood, pH, electricity, heat, and other stimuli. The detachable region may be scored or otherwise designed to incorporate a localized weak region in the filament. The filament may be stretched across a localized region and the filament will break at the weakened point.

It is to be understood that the filament may be broken or severed at a point distal to the catheter end, within the catheter, and perhaps within the container.

The filament may also contain discrete sections along its length to provide information to the doctor or physician. This information or feedback may be provided by incorporating bulges, knots, radio-opaque markers, or other types of discrete sections (or features) along the length of the filament. The discrete sections may be separated by segments of known length. A sensor may be positioned on the distal end of the delivery catheter to monitor the number of segments exiting the delivery catheter. Given the length of each segment, and the number of segments ejected, the total length of filament dispensed from the catheter may be determined. Once a desirable length of filament has been ejected, the filament is cut. The bulges, knots, etc. may also be used to trigger a mechanism that severs the filament.

Applications

As indicated above, containers may hold and introduce vaso-occluding materials to a delivery catheter. The containers may be shipped or delivered to a doctor in a kit form that is ready to be used. Such kits may be designed to include both or either hydrated or unhydrated particles and filaments. Shipping the filaments in a ready-to-use kit minimizes compression of filaments. For example, shipping the filament in a ready-to-use hydrated state minimizes the chance that a filament will break during shipping. Some types of filaments are brittle in their unhydrated state.

Also, the vaso-occluding materials may be packed in particular configurations to optimize packing (e.g., increase packing density). Particles and filaments may be formed in certain shapes (having certain cross sections) such as cubic, hexagonal and triangular so that the particles or filaments interlock and minimize dead space. Spherical and cylindrical shapes may have more dead space when the particles are packed together.

These devices may be used in a wide variety of ways. For example, the vaso-occluding materials may be designed for implantation into the vasculature of a patient. The implantation site may be any site of abnormal blood flow in the patient such as the brain. The abnormal blood flow may be caused by an aneurysm, a ruptured blood vessel, an AVM, a fistula, or a benign or malignant tumor (e.g., cancer or fibroid or the like). Otherwise untreatable tumors are particularly contemplated for treatment by implantation of the vaso-occlusive devices of the invention, as are uterine fibroids and the like. Additionally, the vaso-occlusive devices may be designed for implantation into vessels, ducts and cavities found in the body which are not part of the blood vascular system.

The containers and kits also provide for conveniently hydrating and dispensing particles in a single step. That is, in a single step liquids can be supplied to the container to hydrate the vaso-occluding materials and push them into the delivery catheter. Consequently, there is less likelihood of contamination.

Additionally, various therapeutic liquids may be used with the present invention. The therapeutic liquids are added to the container, purging the first liquid if necessary. Also, the present invention provides for breaking the filaments at certain locations along their lengths. The length of filament ejected may thusly be controlled. Also, graduated lengths of containers may be provided. Each container can include a length of filament corresponding to the size of container.

All publications, patent applications, patents, and other references mentioned herein are incorporated by reference in their entirety. To the extent a conflict in a meaning of a term, or otherwise, the present application will control.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A kit for holding vaso-occluding particles comprising:
   a) a plurality of hydratable vaso-occluding particles; and
   b) a container holding the hydratable vaso-occluding particles, said container having an ingress port adapted for fluid connection with a fluid source and an egress port adapted for fluid connection to a hub of a delivery catheter.

2. The kit of claim 1 wherein the container comprises a chamber to hold said particles and said chamber has a varying cross sectional area.

3. The kit of claim 2 wherein said varying cross sectional area decreases from the ingress port to the egress port.

4. The kit of claim 2 wherein said chamber has a first section and a second section wherein said first section has a first cross sectional area and said second section has a second cross sectional area different than said first cross sectional area.

5. The kit of claim 4 wherein said second cross sectional area decreases towards the fluid egress port.

6. The kit of claim 5 wherein said first cross sectional area is constant.

7. The kit of claim 1 comprising at least one passageway, said passageway being adapted to allow one particle to pass therethrough at a time.

8. The kit of claim 7 wherein said passageway is straight.

9. The kit of claim 7 wherein said passageway is curved.

10. The kit of claim 9 wherein said passageway has one of a spiral or helical shape.

11. The kit of claim 1 further comprising a mixing member, said mixing member being elongate and having a first section outside of said container and a second section within said container for stirring said particles.

12. The kit of claim 11 wherein said second section of said mixing member includes fingers and wherein said mixing member is rotatable.

13. The kit of claim 1 wherein said container comprises a conical distal section, said conical distal section decreasing in diameter and terminating at said fluid egress port.

14. The kit of claim 13 wherein said conical distal section is adapted to fit within a proximal end of a delivery catheter.

15. The kit of claim 1 further comprising a one way valve positioned at at least one of said fluid ingress port and fluid egress port wherein when said one way valve is disposed at said fluid ingress port the valve permits flow only into said container and when said valve is positioned at said fluid egress port said valve permits flow only out of said container.

16. The kit of claim 1 wherein said container further comprises first chamber in fluid communication with said ingress port and a second chamber in fluid communication with said egress port, said first chamber and said second chamber separated by a support member having at least one opening and said at least one opening being larger than said particles such that when said at least one opening is not covered, fluid and said particles may pass through, said container further comprising a movable screen positioned across said support, said screen having at least one particle blocking section and at least one particle passing section, said particle blocking section having a plurality of apertures smaller than said particles and said particle passing section having at least one aperture larger than said particles, said screen being movable such that when said particle passing section of said movable screen is aligned with said opening of said support said particles may enter said second chamber and when said particle passing section of said movable screen member is not aligned with said at least one opening of said support said particles may not enter said second chamber.

17. The kit of claim 1 wherein said container further comprises a fluid outlet and a screen member disposed across said outlet, said screen member having a plurality of apertures and each of said apertures being smaller than said particles such that said particles may not pass through said outlet.

18. The kit of claim 1 wherein said particles comprise polyacrylomtrile.

19. The kit of claim 18 wherein said particles are spherical.

20. The kit of claim 19 wherein said particles have an outer diameter in the range of 40 $\mu$m to 2 mm.

21. The kit of claim 1 further comprising a liquid in said container and wherein said particles are hydrated.

22. The kit of claim 1 further comprising at least one cap covering one of said fluid egress port and fluid ingress port.

23. The kit of claim 1 wherein the ingress port comprises a Luer fitting for connecting said fluid source to said fluid ingress port.

24. The kit of claim 1 further comprising a Luer fitting for connecting to said delivery catheter.

25. The kit of claim 1 wherein said container further comprises at least one fluid relief port and at least one fluid relief passageway connected to said fluid relief port wherein said at least one fluid relief port has a diameter less than the diameter of said particles and wherein liquid driven through said container flows through said chamber and said fluid relief passageway while said particles flow only through said chamber to said fluid egress port.

26. A kit comprising:
   a) a hydratable filamentary occluding material; and
   b) a container holding the filamentary occluding material and having a first opening adapted for connection to a fluid source and a second opening adapted for fluid connection to a hub of a delivery catheter.

27. The kit of claim 26 wherein the first opening is adapted to connect to a fluid source and the second opening is adapted for connection with a delivery catheter.

28. The kit of claim 27 wherein said fluid source is a syringe.

29. The kit of claim 26 wherein said occluding material comprises polyacrylonitrile.

30. The kit of claim 26 wherein said container comprises a passageway and said passageway is adapted to allow only one filament of occluding material to pass through at a time.

31. The kit of claim 30 wherein said filament has a diameter in the range of 100 microns to 5 mm.

32. The kit of claim 30 wherein said passageway is straight.

33. The kit of claim 30 wherein said passageway is curved.

34. The kit of claim 33 wherein said passageway is spiral or helical shaped.

35. The kit of claim 26 wherein said container has a shape selected from the group consisting of disk-, card-, cylindrical-, and turnip-shape.

36. The kit of claim 26 wherein said container further comprises a membrane, said membrane having openings sized to prevent said filament material from passing therethrough but allowing liquid to pass therethrough.

37. The kit of claim 26 wherein the container comprises a rotatable barrel having multiple passageways for holding filaments, and a body having a single ejection channel wherein when one of the multiple passageways is aligned with said single channel a fluid pathway is formed connecting the fluid source to the egress port of the container.

38. The kit of claim 26 further comprising a displacement member for pushing the filament material out the container.

* * * * *